US00PP08729P

United States Patent [19]

Howard, deceased

[11] Patent Number: Plant 8,729

[45] Date of Patent: May 17, 1994

[54] STRAWBERRY PLANT CALLED 'SWEET CHARLIE'

[75] Inventor: Charles M. Howard, deceased, late of Dover, Fla., by Billie L. Howard, executor

[73] Assignee: Florida Foundation Seed Producers, Inc., Greenwood, Fla.

[21] Appl. No.: 936,347

[22] Filed: Aug. 28, 1992

[51] Int. Cl.[5] ..... A01H 5/00
[52] U.S. Cl. ..... Plt./48
[58] Field of Search ..... Plt. 48, 49, 49.1

[56] References Cited

PUBLICATIONS

Voss. 1992. Hortscience 27: 1256–1260.

*Primary Examiner*—James R. Feyrer
*Assistant Examiner*—Elizabeth C. Kemmerer
*Attorney, Agent, or Firm*—William M. Hobby, III

[57] ABSTRACT

A new and distinct strawberry variety which originated from seed produced by a hand-pollinated cross between FL 80-456 and Pajaro, is provided. The new strawberry is distinguished by its earliness of production, its cupped leaves, its reponse to pests, and its sweet fruit.

1 Drawing Sheet

SUMMARY OF THE INVENTION

A new and distinct variety of strawberry originated from a hand pollinated cross of FL 80-456, an anthracnose-resistant (Colletotrichum spp.) clone, and Pajaro (a 1980 strawberry release from the University of California) and has been asexually propagated by runners at the University of Florida, Agricultural Research and Education Center, Dover, Fla. The seeds resulting from the controlled hybridization were germinated in a greenhouse and the resulting seedlings were planted and allowed to produce daughter plants (by asexual propagation). Two daughter plants from each seedling were transplanted to raised beds. These plants later fruited and one pair was selected from its outstanding fruit quality and high yield. The new variety, FL 85-4925, has been asexually propagated by runners annually and further test plantings have established that during asexual multiplication, the vegetative and fruit characteristics of the original plants are maintained. The new strawberry, called "Sweet Charlie", is distinguished by its earliness of producing its cupped leaves, its response to pests, and its sweet fruit.

BRIEF DESCRIPTION OF THE PHOTOGRAPHS

The accompanying photographs show typical specimens of the fruit and leaves of the new variety in color.

DETAILED DESCRIPTION OF THE NEW VARIETY

Figure 1:
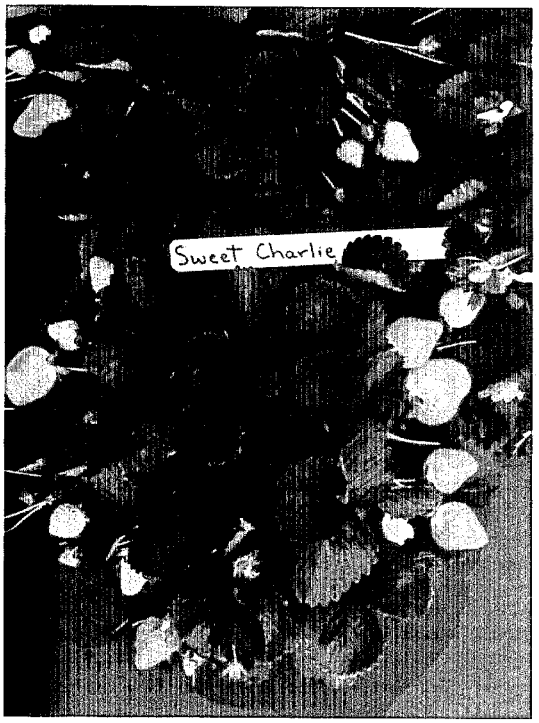
FIG. 1 is a photograph of the present strawberry plant.
Figure 2:
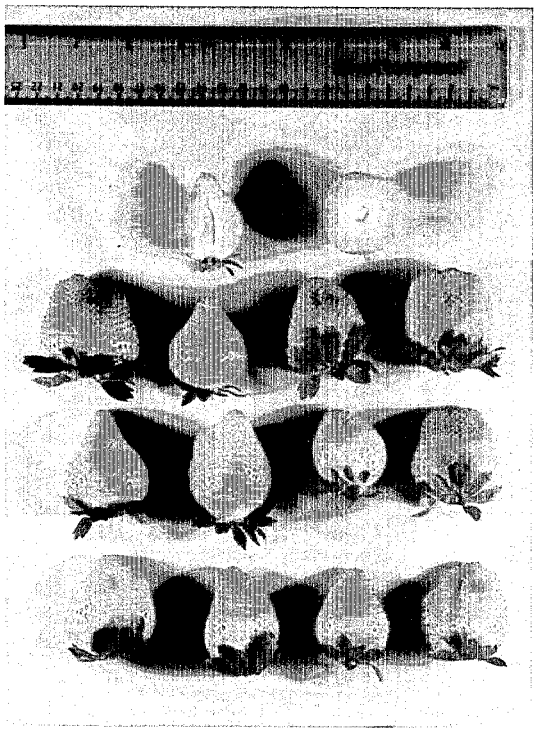
FIG. 2 is a photograph of pieces of fruit from the present strawberry plant.

The following is a detailed description of the pomological characteristics of the subject strawberry. Where dimensions, sizes, colors, and other characteristics are given, it is to be understood that such characteristics are approximations of averages set forth as accurately as practicable. The pedigree of the present strawberry (FL 85-4925) is from a cross of FL 80-456, , an anthracnose-resistant clone and Pajaro, a 1980 strawberry release from the University of California, which is extremely susceptible to anthracnose fruit rot. FL 80-456 is a cross between FL 77-163 and FL 78-1832. FL 78-1832 is a cross between Dover and LA-2556. Pajaro is a cross between Sequoia and 63.7-101.

The description reported herein is from specimens grown at Dover, Fla.

Type: Short day The strawberry is described as an early fruiting short-day type because it produces fruit earlier in the season (i.e., from December through February) than does the Pajaro or Oso Grande strawberries.

Size: Medium (smaller and more compact than Oso Grande). The plants are measured in a fruiting field in May range in height from 19 to 26 cm, and width from 29 to 42 cm.

Productivity: Medium-high (22–34 MT/ha) The seasonal fruit yield (overall productivity) is generally less than that of Oso Grande strawberry. The strawberry has been a good plant-maker (stolen producer) in the nursery (similar to Oso Grande), yet tends to produce fewer stolens than Oso Grande in the fruit production field, a desirable characteristic. Runner control, by pruning, is required to maximize productivity. This strawberry is not adapted for mechanical harvest.

Leaves: Petioles range in length from 75 to 100 mm and are stiff with numerous hairs. Leaflets are generally cupped, medium to dark green ($L^*=31.4$, $a^*=4.7$, $b^*=5.4$ [$L^*a^*b^*$ color notation system]) (Munsell 7.56Y 3/1), semiglossy, scabrous, and obovate. The central leaflet has an obtuse base while the side leaflets have oblique bases. The length of mature leaflets varies from 58 to 80 mm; the width from 65 to 78 mm. Leaflet margins are rounded dentate, with 21 to 23 serrations per leaflet. The bottom of the leaves are yellow green, Munsell 5GY 5/3).

Flowers and fruit: Flowers open at or below canopy height. Pedicels attached to mature primary fruit are 100 to 130 mm long, with branching of the inflorescence usually occurring very close to the crown. Primary fruit are generally wedge shaped; secondary and later fruit are conical to wedge shaped. External fruit color is orange red ($L^*=36.2$, $a^*=30.3$, and $b^*=43.6$); internal color is orange streaked with white. The skin color of the fruit is more orange (Munsell 5YR 4/10) than is that of Pajaro, Oso Grande, or Grace strawberries. The achenes are greenish yellow and slightly recessed. Calyx lobes are 20 to 25 mm long and coarsely serrated. Ripe fruit are firm, similar to Oso Grande, have a vitamin C concentration of 53 mg/100 g FW, and an average berry weight of 17 g. The fruit has a distinctively sweet flavor due to a relatively high sugar/acid ratio. Typical dimensions of the berries harvested in mid March are 5.0 cm length and 4.3 cm breadth for primary fruit, and 4.3 cm length and 3.6 cm breadth for secondary fruit. The fruit has a tendency to show bruises after precooling more readily than does Oso Grande, and, for this reason, may not be suitable for long distance shipment. The plant is resistant to anthracnose fruit rot which contrast to Pajaro which is extremely susceptible to anthracnose fruit rot.

Pest responses: Moderate resistance to anthracnose crown and fruit rot, powdery mildew, and twospotted spider mite; susceptible to Botrytis fruit rot and Phomopsis leaf blight. The plant appears to be highly resistant to anthracnose fruit rot caused by C. acutatum Simmonds. The strawberry is more resistant to anthracnose crown and fruit rot, but less resistant to Phomopsis fruit rot, than is Pajaro or Oso Grande.

Asexual reproduction: The plant has been asexually reproduced primarily by rooting of cuttings but has been reproduced by budding. The recommended planting date is early to mid October. Plants start to flower in early to mid November, and the harvest season generally lasts from early December until early April.

Distinctive features: The most distinctive features of the variety are its earliness of production (for a short day type), its anthracnose crown and fruit rot resistance, and the sweet flavor of its fruit.

DNA comparison: A comparison of three varieties of strawberries, Sweet Charlie, Pajaro, and Oso Grande using the United States Dept. of Agricultures RAPD protocol was made for a comparison of the varieties at the DNA level. Different banding patterns indicated the difference in DNA sequences using two different primers (#564 and #534 from the University of British Columbia). The three varieties yielded distinct, easily distinguishable DNA fragments.

Table I below shows a comparison of postharvest composition and quality of several strawberry cultivars. Sweet Charlie is compared with Oso Grande and Selva for ascorbic acid levels, percent of soluble solids, percent of titratable acids, pH and texture before storage and again after one week storage at 7° C.

TABLE 1

Comparison of postharvest composition and quality of several strawberry cultivars.

| Cultivar | % FW Loss | mg/100 g FW Ascorbic Acid | % FW Soluble Solids | % FW Titratable Acid | pH | Texture (N) |
|---|---|---|---|---|---|---|
| Before Storage | | | | | | |
| Sweet Charlie | | 52.63 a[y] | 7.0 a | 0.664 b | 3.58 a | 7.25 b |
| Oso Grande | | 34.43 b | 4.6 c | 0.690 a | 3.63 a | 8.13 b |
| Selva | | 40.23 b | 6.0 b | 0.984 a | 3.49 b | 10.99 a |
| 1 week at 7° C. | | | | | | |
| Sweet Charlie | 7.76 a | 56.43 a | 6.7 a | 0.651 b | 3.75 a | 6.93 b |
| Oso Grande | 12.05 a | 40.46 b | 5.3 b | 0.846 ab | 3.58 b | 7.80 b |
| Selva | 9.96 a | 44.03 b | 5.9 b | 0.965 a | 3.61 b | 10.20 a |

[y]Mean separation within columns by Duncan's multiple range test, P = 0.05.

Table II shows the yield and average fruit size of several strawberry cultivars and compares Sweet Charlie with Oso Grande, Pajaro and Selva as to marketable yield, cull yield, and as to size.

TABLE 2

Yield and average fruit size of several strawberry cultivars at AREC-Dover.[z,y]

| Cultivars | Marketable yield (flats/acre)[x] 87–88 | 89–90 | 90–91 |
|---|---|---|---|
| Sweet Charlie | 3157a | 1755b | 530ab[w] |
| Oso Grande | — | 2301a | 421b |
| Pajaro | 2509b | 1129c | — |
| Selva | 1964c | 1615b | 596a |
| **Cultivars** | **Cull yield (flats/acre) 87–88** | **89–90** | **90–91** |
| Sweet Charlie | 665a | 561a | 90b |
| Oso Grande | — | 826a | 52b |
| Pajaro | 632a | 583a | — |
| Selva | 393b | 452a | 151a |
| **Cultivars** | **Size (g/fruit) 87–88** | **89–90** | **90–91** |
| Sweet Charlie | 17a | 16c | 20a |
| Oso Grande | — | 20a | 19a |
| Pajaro | 17a | 18b | — |
| Selva | 15b | 15c | 14b |

[z]This data was taken from Albregts et al. 1989 and 1990 and Chandler et al. 1992.
[y]Mean separation within columns by Duncan's multiple range test, P = 0.05.
[x]One flat = 4.65 kg.

It is claimed:

1. A new and distinct variety of strawberry plant, substantially as illustrated and described, characterized by its earliness of production, disease resistance, and the sweet flavor of its fruit.

* * * * *